(12) United States Patent
Kim

(10) Patent No.: US 10,301,686 B2
(45) Date of Patent: May 28, 2019

(54) **SELECTIVE DETECTION METHOD FOR *MYCOBACTERIUM TUBERCULOSIS* AND NONTUBERCULOUS MYCOBACTERIA AND KIT USING SAME**

(71) Applicant: HYUNIL-BIO CO., Gangneung-si (KR)

(72) Inventor: Jeong Uk Kim, Gangneung-si (KR)

(73) Assignee: HYUNIL-BIO CO., Gangneung-si (KR)

( * ) Notice: Subject to any disclaimer, the term of this patent is extended or adjusted under 35 U.S.C. 154(b) by 685 days.

(21) Appl. No.: 14/778,410

(22) PCT Filed: Mar. 19, 2014

(86) PCT No.: PCT/KR2014/002310
§ 371 (c)(1),
(2) Date: Sep. 18, 2015

(87) PCT Pub. No.: WO2014/148817
PCT Pub. Date: Sep. 25, 2014

(65) Prior Publication Data
US 2016/0281141 A1    Sep. 29, 2016

(30) Foreign Application Priority Data
Mar. 21, 2013 (KR) .................. 10-2013-0030409

(51) Int. Cl.
*C12Q 1/68* (2018.01)
*C12Q 1/689* (2018.01)

(52) U.S. Cl.
CPC ......... *C12Q 1/689* (2013.01); *C12Q 2600/16* (2013.01)

(58) Field of Classification Search
None
See application file for complete search history.

(56) References Cited

U.S. PATENT DOCUMENTS 5,851,761 A * 12/1998 McAdam .............. C12Q 1/689
435/6.11

FOREIGN PATENT DOCUMENTS

| CN | 102154525 A | 8/2011 |
| KR | 1020030075315 | 9/2003 |
| KR | 1020120113119 | 10/2012 |
| KR | 1020130008283 | 1/2013 |
| WO | WO-96/41005 A1 | 12/1996 |
| WO | WO 2006/136621 A1 | 12/2006 |
| WO | WO-2011/148280 A1 | 12/2011 |
| WO | WO-2011/149305 A2 | 12/2011 |
| WO | WO-2012/002598 A1 | 1/2012 |

OTHER PUBLICATIONS

Feazel et al. (PNAS, 2009, 106(38):16393-16399).*
Gingeras et al. (1998, Genome Res. 8 (5), 435-448) (Year: 1998).*
Roesch et al. (2009, Open Microbiol J 3, 40-46) (Year: 2009).*
Lowe et al. (Nucleic Acids Research, 1990, 18(7):1757-1761) (Year: 1990).*
Fyfe et al. (Appl Environ Microbiol, 2007, 73(15):4733-4740) (Year: 2007).*
Lazzeri et al., "Novel primer-probe sets for detection and identification of mycobacteria by PCR-microarray assay," J. Clin. Microbiol. 50(11):3777-3779 (2012).
Lira et al., "Evaluation of a IS6110-Taqman real-time PCR assay to detect *Mycobacterium tuberculosis* in sputum samples of patients with pulmonary TB," J. Appl. Microbiol. 114(4):1103-1108 (2013).
International Search Report for PCT/KR2014/002310, dated Jun. 25, 2014 (2 pages).

* cited by examiner

*Primary Examiner* — Stephanie K Mummert
(74) *Attorney, Agent, or Firm* — Clark & Elbing LLP; Susan M. Michaud

(57) ABSTRACT

The present invention relates to a method for specifically detecting *Mycobacterium tuberculosis* and nontuberculous mycobacteria by simultaneously amplifying and analyzing target genes using various primers and probes, and a kit using same. The method of the present invention is capable of selectively detecting *Mycobacterium tuberculosis* and nontuberculous mycobacteria with very high efficiency through a multiplex real-time polymerase chain reaction (PCR) using probes and primers specific to target genes (particularly, IS6110, 16S rRNA and β-actin). Also, the kit of the present invention is capable of conveniently and efficiently detecting the target genes in a sample through a multiplex real-time PCR. Therefore, the method and the kit of the present invention are capable of selectively detecting with ease whether or not there is an infection with *Mycobacterium tuberculosis* or nontuberculous mycobacteria in a sample, and can be more accurately applied to the treatment of diseases on the basis thereof.

6 Claims, 3 Drawing Sheets
Specification includes a Sequence Listing.

SELECTIVE DETECTION METHOD FOR *MYCOBACTERIUM TUBERCULOSIS* AND NONTUBERCULOUS MYCOBACTERIA AND KIT USING SAME

TECHNICAL FIELD

The present invention relates to a method for selectively detecting *Mycobacterium tuberculosis* and nontuberculous mycobacteria in samples through the simultaneous amplification and analysis of a target gene, and a kit using the same.

BACKGROUND ART

Nontuberculous mycobacteria, which are all mycobacteria except *Mycobacterium tuberculosis* and *Mycobacterium leprae*, are known to cover approximately 140 species and are widely found in natural environments, such as soils and water. However, as searches regarding acquired immune deficiency syndrome (AIDS) epidemic from the 1980s reported that the *Mycobacterium* strains are the main causative bacteria of opportunistic infections of AIDS patients and may cause severe pulmonary diseases as well as infections in normal patients, and the clinical importance thereof is growing.

Recently, the USA and many European countries, which have a low prevalence of tuberculosis, have seen an increase in the incidence of infections caused by nontuberculous mycobacteria. Also in Korea, infections by nontuberculous mycobacteria have increased although the incidence of tuberculosis has been reduced. In addition, tuberculosis is still one of the most serious health problems globally, and the incidence of tuberculosis in Korean is very high with 78.9 cases per 100,000 people in 2011.

Owing to a policy that granted medical insurance for the performing of liquid culture of tuberculosis bacteria in 2009 in Korea, there was an increase in the number of laboratories designed to perform liquid culture. The liquid culture detects nontuberculous mycobacteria more often than does the solid culture of the conventional art. According to recent reports, nontuberculous mycobacteria were isolated in about 12% of smear/culture-positive *Mycobacterium tuberculosis* cases, and nontuberculous mycobacteria isolated from the sputum account for about 10-20% of pulmonary disease cases in Japan, Hong Kong, and Korea, and about 40-50% of pulmonary disease in the USA, Canada, and West Europe. In particular, it has been reported that mycobacteria isolated from clinical specimens, containing nontuberculous mycobacteria, accounted for about 33% of cases in 1979-1980 and about 75% of cases in 1992 in the USA.

Most of all, the pulmonary disease by nontuberculous mycobacteria is prone to be misdiagnosed due to the likeness to slowly advanced pulmonary disease. However, drugs that are sensitive to *Mycobacterium tuberculosis* and nontuberculous mycobacteria are different, and therefore, there is a growing demand for developing a prompt and accurate selective detection method of *Mycobacterium tuberculosis* and nontuberculous mycobacteria.

However, the currently marketable test reagents used to detect *Mycobacterium tuberculosis* and nontuberculous mycobacteria are problematic in view of the accuracy in detection and diagnosis since the test reagents employ nucleotide sequences that are unique to nontuberculous mycobacteria, as well as nucleotide sequences also present in *Mycobacterium tuberculosis*. As a result, *Mycobacterium tuberculosis* within a particular concentration range reacts only with nontuberculous mycobacteria detection primer without reacting with *Mycobacterium tuberculosis* detection primer, so *Mycobacterium tuberculosis* is wrongly identified as nontuberculous mycobacteria, or only nontuberculous mycobacteria are detected when nontuberculous mycobacteria and *Mycobacterium tuberculosis* are simultaneously present.

In addition, there are significant differences in the pathophysiological and epidemiological characteristics between *Mycobacterium tuberculosis* and nontuberculous mycobacteria. For example, *Mycobacterium tuberculosis* is infectious between persons, but nontuberculous mycobacteria are not infectious between persons. Therefore, *Mycobacterium tuberculosis* needs to be detected selectively from nontuberculous mycobacteria. In addition, since respective species of nontuberculous mycobacteria have a great variety of pathogenicity, the nontuberculous mycobacteria need to be specifically identified to select appropriate therapeutic medicines. In addition, the conventional mycobacteria culture and identification tests have the disadvantage of taking 2-4 weeks.

Accordingly, prompt and accurate selective detection methods of *Mycobacterium tuberculosis* and nontuberculous mycobacteria using a primer set and/or probe, capable of recognizing unique nucleotide sequences present in nontuberculous mycobacteria but not *Mycobacterium tuberculosis*, are urgently required.

Throughout the entire specification, many papers and patent documents are referenced and their citations are represented. The disclosure of cited papers and patent documents are entirely incorporated by reference into the present specification, and the level of the technical field within which the present invention falls, and details of the present invention are explained more clearly.

DETAILED DESCRIPTION OF THE INVENTION

Technical Problem

The present inventors have endeavored to develop a method capable of selectively detecting *Mycobacterium tuberculosis* and nontuberculous mycobacteria. As a result, the present inventors have verified that *Mycobacterium tuberculosis* and nontuberculous mycobacteria can be specifically and simply detected from a sample (e.g., sputum, blood, saliva, or urine) by preparing primers and probes capable of specifically detecting IS6110 gene of *Mycobacterium tuberculosis* and 16S rRNA gene of nontuberculous mycobacteria and performing multiplex real-time PCT, and have then completed the present invention.

Therefore, the present invention has been made in view of the above-mentioned problems, and an aspect of the present invention is to provide a selective detection method for *Mycobacterium tuberculosis* and nontuberculous mycobacteria.

Another aspect of the present invention is to provide a selective detection kit for *Mycobacterium tuberculosis* and nontuberculous mycobacteria.

Still another aspect of the present invention is to provide a nucleotide sequence for detecting nontuberculous mycobacteria.

Still another aspect of the present invention is to provide a probe for detecting nontuberculous mycobacteria.

Other purposes and advantages of the present disclosure will become more obvious with the following detailed description of the invention, claims, and drawings.

Technical Solution

In accordance with an aspect of the present invention, there is provided a selective detection method of *Mycobacterium tuberculosis* and nontuberculous mycobacteria, the method including: (a) preparing a sample; (b) amplifying a target nucleotide sequence in the sample using: (i) a *Mycobacterium tuberculosis* detection set comprising a primer pair including a primer of SEQ ID NO: 1 and a primer of SEQ ID NO: 2, and at least one probe selected from the group consisting of SEQ ID NO: 3 and SEQ ID NO: 4; and (ii) a nontuberculous mycobacteria detection set comprising a primer pair including at least one primer selected from the group consisting of SEQ ID NO: 5, SEQ ID NO: 6, and SEQ ID NO: 7 and a primer of SEQ ID NO: 8, and at least one probe selected from the group consisting of SEQ ID NO: 9 and SEQ ID NO: 10; and (c) analyzing results of the amplification.

In accordance with another aspect of the present invention, there is provided a kit for the selective detection of *Mycobacterium tuberculosis* and nontuberculous mycobacteria, the kit including: (i) a *Mycobacterium tuberculosis* detection set comprising a primer pair including a primer of SEQ ID NO: 1 and a primer of SEQ ID NO: 2, and at least one probe selected from the group consisting of SEQ ID NO: 3 and SEQ ID NO: 4; and (ii) a nontuberculous mycobacteria detection set comprising a primer pair including at least one primer selected from the group consisting of SEQ ID NO: 5, SEQ ID NO: 6, and SEQ ID NO: 7 and a primer of SEQ ID NO: 8, and at least one probe selected from the group consisting of SEQ ID NO: 9 and SEQ ID NO.

In accordance with still another aspect of the present invention, there is provided a nucleotide sequence for detecting nontuberculous mycobacteria, including a nucleotide sequence selected from the group consisting of SEQ ID NO: 5, SEQ ID NO: 6, and SEQ ID NO: 7.

In accordance with still another aspect of the present invention, there is provided a probe for detecting nontuberculous mycobacteria, including a nucleotide sequence selected from the group consisting of SEQ ID NO: 9 and SEQ ID NO: 10.

The present inventors have endeavored to develop a method capable of selectively detecting *Mycobacterium tuberculosis* and nontuberculous mycobacteria. As a result, the present inventors have verified that *Mycobacterium tuberculosis* and nontuberculous mycobacteria can be specifically and simply detected from the sample (e.g., sputum, blood, saliva, or urine) by preparing primers and probes capable of specifically detecting IS6110 gene of *Mycobacterium tuberculosis* and 16S rRNA gene of nontuberculous mycobacteria and performing multiplex real-time PCT.

The method of using primers and probes, according to the present invention, can selectively detect *Mycobacterium tuberculosis* and nontuberculous mycobacteria in samples very simply and effectively.

According to a certain embodiment of the present invention, the amplification of the present invention is performed according to polymerase chain reaction (PCT). According to a certain embodiment of the present invention, the primers of the present invention are used in gene amplification reactions.

As used herein, the term "amplification reaction" refers to a reaction of amplifying nucleic acid molecules. A variety of amplification reactions have been reported in the art, and include polymerase chain reaction (PCR, U.S. Pat. Nos. 4,683,195, 4,683,202, and 4,800,159), reverse transcription-polymerase chain reaction (RT-PCR, Sambrook et. al., Molecular Cloning. A Laboratory Manual, 3rd ed. Cold Spring Harbor Press (2001)), Miller, H. I. (WO 89/06700) and Davey, C. et. al., (EP 329,822), multplex PCR (McPherson and Moller, 2000), ligase chain reaction (LCR) (17, 18), Gap-LCR (WO 90/01069), repair chain reaction (EP 439, 182), transcription-mediated amplification (TMA) (19) (WO 88/10315), self sustained sequence replication (20) (WO 90/06995), selective amplification of target polynucleotide sequences (U.S. Pat. No. 6,410,276), consensus sequence primed polymerase chain reaction (CP-PCR, U.S. Pat. No. 4,437,975), arbitrarily primed polymerase chain reaction (AP-PCR, U.S. Pat. Nos. 5,413,909, and 5,861,245), nucleic acid sequence based amplification (NASBA, U.S. Pat. Nos. 5,130,238, 5,409,818, 5,554,517, and 6,063,603), strand displacement amplification (21, 22), and loop-mediated isothermal amplification (LAMP) (23), but are not limited thereto. The other usable amplification methods are disclosed in U.S. Pat. Nos. 5,242,794, 5,494,810, and 4,988,617, and U.S. patent Ser. No. 09/854,317.

As used herein, the term "primer" refers to an oligonucleotide, and the primer may act as an initial point of synthesis in the conditions where the synthesis of the primer elongation products that are complementary to a nucleic acid chain (template) is induced, that is, the presence of nucleotides and polymerases such as DNA polymerases, and appropriate temperature and pH values. Preferably, the primer includes deoxyribonucleotides, and has a single chain. The primer used herein may include naturally occurring dNMPs (that is, dAMP, dGMP, dCMP, and dTMP), modified nucleotides, or non-naturally occurring nucleotides. Also, the primer may include ribonucleotides.

The primer needs to be long enough to prime the synthesis of elongation products in the presence of polymerases. The appropriate length of the primer varies depending on several factors, such as temperature, field of application, and primer source. The term "annealing" or "priming" refers to the apposition of oligodeoxynucleotide or nucleic acid to the template nucleic acid. The apposition enables the polymerase to polymerize nucleotides to form a nucleic acid molecule which is complementary to the template nucleic acid or a portion thereof.

PCR is the most well known method of nucleic acid amplification, and modifications and applications thereof have been developed. For example, in order to improve the specificity or sensitivity of PCR, touchdown PCR, hot start PCR, nested PCR, and booster PCR were developed by modifying the conventional PCR procedure. Further, multiplex PCR, real-time PCR, differential display PCR (DD-PCR), rapid amplification of cDNA ends (RACE), inverse polymerase chain reaction (IPCR), vectorette PCR, and thermal asymmetric interlaced PCR (TAIL-PCR) were developed for specific applications. Detailed descriptions of PCR are shown in McPherson, M. J., and Moller, S. G. PCR. BIOS Scientific Publishers, Springer-Verlag New York Berlin Heidelberg, N.Y. (2000), the teaching of which is incorporated by reference herein.

In cases where the method of the present invention is conducted using primers, target genes can be simultaneously detected from targets of analysis (e.g., sputum, blood, saliva, or urine as a target-derived sample) by performing gene amplification reactions. Therefore, in the present invention, the gene amplification reaction is performed using primers binding to DNA extracted from the sample.

The extraction of DNA from the sample may be performed according to the conventional methods known in the art. (See: Sambrook, J. et al., Molecular Cloning. A Laboratory Manual, 3rd ed. Cold Spring Harbor Press (2001);

Tesniere, C. et al., Plant Mol. Biol. Rep., 9:242(1991); Ausubel, F. M. et al., Current Protocols in Molecular Biology, John Willey & Sons (1987); and Chomczynski, P. et al., Anal. Biochem. 162:156(1987)).

The primer used herein is hybridized or annealed with one region of the template to form a double-chain structure. The hybridization conditions suitable for forming double-chain structures are disclosed in Joseph Sambrook, et al., Molecular Cloning, A Laboratory Manual, Cold Spring Harbor Laboratory Press, Cold Spring Harbor, N.Y. (2001), and Haymes, B. D., et al., Nucleic Acid Hybridization, A Practical Approach, IRL Press, Washington, D.C. (1985).

Various DNA polymerases may be used in the amplification of the present invention, and include the "Klenow" fragment of E. coli DNA polymerase I, thermostable DNA polymerase, and bacteriophage T7 DNA polymerase. Specifically, the polymerase is thermostable DNA polymerase that can be obtained from a variety of bacteria species, and includes Thermus aquaticus (Taq), Thermus thermophilus (Tth), Thermus filiformis, Thermis flavus, Thermococcus literalis, and Pyrococcus furiosus (Pfu).

It is preferable to provide excessive amounts of components necessary for the reaction in a reaction container when the polymerization reaction is performed. The excessive amounts of components necessary for the amplification reaction are such that the amplification reaction is not substantially restricted by the concentrations of the components. It is desirable to supply cofactors, such as $Mg^{2+}$, and dATP, dCTP, dGTP and dTTP to the reaction mixture to such an extent that the degree of amplification can be achieved. All the enzymes used in the amplification reaction may be in an active state under the same reaction conditions. In fact, the buffer enables all the enzymes to approach the optimum reaction conditions. Therefore, the amplification procedure of the present invention may be performed in a single reaction material without changing conditions, such as the addition of reaction materials.

The annealing herein is performed under the strict conditions that allow specific combination between target nucleotide sequences and primers. The strict conditions for annealing are sequence-dependent and vary depending on surrounding environmental variables.

The thus amplified target genes (specifically, IS6110 and 16S rRNA) are analyzed by appropriate methods to selectively detect Mycobacterium tuberculosis and nontuberculous mycobacteria. For example, target genes can be detected by subjecting the foregoing amplification reaction products to gel electrophoresis and observing and analyzing the resultant bands.

Therefore, when the method of the present invention is conducted based on the amplification reaction using DNA, Mycobacterium tuberculosis and nontuberculous mycobacteria can be detected or quantified in the DNA extracted from a sample, wherein the method includes the steps of: (i) performing an amplification reaction using a primer pair and a probe annealed to the IS6110 nucleotide sequence; and a primer pair and a probe annealed to the 16S rRNA nucleotide sequence; and (ii) analyzing products of the amplification reaction through fluorescence.

According to the present invention, examples of the nontuberculous mycobacteria strain detectable by the method of the present invention include M. abscessus ATCC 19977, M. acapulcensis KCTC 9501, M. africanum ATCC 25420, M. agri KCTC 9502, M. alvei KCTC 19709, M. asiaticum KCTC 9503, M. aurum KCTC 19457, M. austroafricanum KCTC 9504, M. avium ATCC 25291, M. bolletii KCTC 19281, M. botniense KCTC 19646, M. bovis ATCC 19210, M. brumae KCTC 19711, M. celatum ATCC 51131, M. chelonae subsp chelonae KCTC 9505, M. chlorophenolicum KCTC 19089, M. chubuense KCTC 19712, M. diernhoferi KCTC 9506, M. fallax KCTC 9508, M. flavescens ATCC 14474, M. fortuitum ATCC 6841, M. frederiksbergense KCTC 19100, M. gadium ATCC 27726, M. gastri ATCC 15754, M. gilvum KCTC 19423, M. goodii ATCC BAA-955, M. gordonae KCTC 9513, M. haemophilum ATCC 29548, M. hassiacum ATCC 700660, M. interjectum ATCC 51457, M. intermedium ATCC 51848, M. intracellulare ATCC 13950, M. intracellulare KCTC 9514, M. kansasii ATCC 12478, M. lentiflavum KMRC 70087, M. malmoense ATCC 29571, M. mantobense KCTC 9977, M. marinum ATCC 927, M. massiliense KCTC 19086, M. microti ATCC 19422, M. moriokaense KCTC 9516, M. mucogenicum KCTC 19088, M. neoaurum KCTC 19096, M. nonchromogenicum ATCC 19530, M. obuense KCTC 19097, M. parascrofulaceum KCTC 9979, M. peregrinum KCTC 9615, KMRC 75002, M. phlei KCTC 9689, M. porcinum KCTC 9517, M. pulveris KCTC 9518, M. scrofulaceum ATCC 19981, M. septicum ATCC 700731, M. simiae ATCC 25275, M. shimoidei ATCC 27962, M. smegmatis KCTC 9108, M. szulgai KCTC 9520, KMRC 31125, M. terrae KCTC 9614, M. triplex ATCC 700071, M. triviale KMRC 70093, M. tuberculosis ATCC 25177, ATCC 27294, M. ulcerans ATCC 19423, M. vaccae KCTC 19087, M. vanbaalenii KCTC 9966, M. wolinskyi ATCC 700010, and M. xenopi KMRC 42001, but are not limited thereto.

As used herein, the term "hybridization" refers to the formation of a duplex structure by pairing complementary nucleotide sequences of two single-strand nucleic acids. The hybridization may occur when complementarity between single-strand nucleic acid sequences is perfectly matched or even when some mismatch bases are present. The degree of complementarity required for hybridization may vary depending on the hybridization reaction conditions, and may be controlled by, particularly, the temperature. The terms "annealing" and "hybridization" are not substantially differentiated from each other, and thus are used together.

According to a certain embodiment, the method and kit of the present invention can perform real-time PCR of simultaneously detecting three genes (IS6110, 16S rRNA, and β-actin) to differentiate Mycobacterium tuberculosis and nontuberculous mycobacteria from other microorganisms.

According to a certain embodiment, the method and kit of the present invention includes: (i) a Mycobacterium tuberculosis detection set composed of a primer pair including a primer of SEQ ID NO: 1 and a primer of SEQ ID NO: 2, and at least one probe selected from the group consisting of SEQ ID NO: 3 and SEQ ID NO: 4; (ii) a nontuberculous mycobacteria detection set composed of a primer pair including at least one primer selected from the group consisting of SEQ ID NO: 5, SEQ ID NO: 6, and SEQ ID NO: 7 and a primer of SEQ ID NO: 8, and at least one probe selected from the group consisting of SEQ ID NO: 9 and SEQ ID NO: 10; and (iii) a β-actin detection set, as an internal control, composed of a primer pair including a primer of SEQ ID NO: 11 and a primer of SEQ ID NO: 12, and a probe of SEQ ID NO: 13.

According to a certain embodiment, the target gene used in the method and kit of the present invention includes: the IS6110 gene detected by a primer pair including a primer of SEQ ID NO: 1 and a primer of SEQ ID NO: 2, and at least one probe selected from the group consisting of SEQ ID NO: 3 and SEQ ID NO: 4; the 16S rRNA gene detected by a primer pair including at least one primer selected from the group consisting of SEQ ID NO: 5, SEQ ID NO: 6, and SEQ ID NO: 7 and a primer of SEQ ID NO: 8, and at least one probe selected from the group consisting of SEQ ID NO: 9 and SEQ ID NO: 10; and the β-actin gene detected by a primer pair including a primer of SEQ ID NO: 11 and a primer of SEQ ID NO: 12, and a probe of SEQ ID NO: 13.

Real-time PCR is the technique of analyzing an increase in PCT amplification product through real-time monitoring. During the exponential phase in which the increase in PCR product is proportional to the initial amount of target template, the emission amount of fluorescence for each cycle may be recorded to monitor the PCR reaction. A higher start copy number of the target nucleic acid enables the increase in fluorescence to be observed more quickly, resulting in lower cycle threshold (Ct) values. A distinctive increase in fluorescence higher than the reference value measured during 3-15 cycles means the detection of accumulated PCR products. Real-time PCR has the following advantages when compared with conventional PCR methods: (a) the real-time PCR can obtain data during the exponential growth phase while the conventional PCR performs a measurement in the plateau phase; (b) the increase in report fluorescence signals is directly proportional to the number of generated amplicons; (c) the degraded probe provides a permanent record amplification of amplicons; (d) the detection range is increased; (e) the required nucleic acids are 1,000 times less than as in the conventional PCR method; (f) the amplified DNA can be detected without the separation through electrophoresis; (g) the increased amplification efficiency can be obtained using small amplicon sizes; and (h) the risk of contamination is low.

When the amount of PCR amplification product reaches the amount detectable by fluorescence, the amplification curve occurs, and the signal rises in an exponential manner and reaches the plateau phase. The increase in initial DNA decreases the number of cycles at which the amount of amplification product reaches the detectable amount, and thus, the amplification curve appears quickly. Therefore, in cases where real-time PCR is performed using a reference sample that is diluted by stages, amplification curves which are disposed at the same intervals in the order of amount of initial DNA. Here, the threshold is set at an appropriate point, thereby calculating the Ct value, which is the cross point of the threshold and the amplification curve.

In the real-time PCR, PCR amplification products are detected through fluorescence. There are an interchelating method (SYBR green I method), a method using a fluorescence-labeled probe (TaqMan probe method), and the like in the detection method. According to the interchelating method, all the double-stranded DNAs are detected, and thus a reaction system can be constructed at low costs without preparing probes for respective genes. The method using a fluorescence-labeled probe requires high costs, but can differentiate and detect even similar sequences due to high detection specificity. According to a certain embodiment, the method and kit of the present invention employs a TaqMan probe method.

First, the interchelating method, which uses a double-strand DNA binding dye, quantifies the production of amplicons including non-specific amplification products and primer-dimer complexes by using a non-sequence specific fluorescence interchelating reagent (SYBR green I or ethidium bromide). The reagent does not bind to ssDNA. SYBR green I is a fluorescent dye binding to a minor groove of the double-strand DNA, and is an interchelator that hardly displays fluorescence in the solution but display strong fluorescence when binding to double-strand DNA (Morrison T B, Biotechniques., 24(6): 954-8, 960, 962(1998)). Therefore, the fluorescence is emitted through the binding between SYBR green I and double-strand DNA, thereby measuring the amount of the amplified products produced. SYBR green real-time PCR is accompanied by an optimization procedure, such as melting point analysis or dissociation curve analysis, for amplicon identification. SYBR green is normally used in the singleplex reaction, but may be used in the multiplex reaction if accompanied by the melting curve analysis (Siraj A K, et al., Clin Cancer Res., 8(12): 3832-40(2002); and Vrettou C., et al., Hum Mutat., Vol 23(5): 513-521(2004)).

The cycle threshold (Ct) value means the number of cycles required for the detection of fluorescence signal, which is generated in a reaction, to exceed a threshold, and this value is inversely proportional to an algebraic number of the initial copy number. Hence, the Ct value assigned to a specific well reflects on the number of cycles in which a sufficient number of amplicons are accumulated. The Ct value is the cycle in which an increase in ΔRn is first detected. Rn means the intensity of fluorescent signal generated during PCR at each time point, and Rn means the fluorescence emission intensity (normalized reporter signal) of the reporter dye divided by the fluorescence emission intensity of the reference dye. The Ct value is also called the crossing point (Cp) for the light cycler. The Ct value indicates the time point at which a system starts to detect an increase in fluorescence signal related to the exponential growth of PCR product in the long-linear phase. This period provides the most useful information about the reaction. The slope of the log-linear phase indicates amplification efficiency (Eff) (http://www.appliedbiosystems.co.kr/).

Meanwhile, TaqMan probe is typically an oligonucleotide that contains a fluorophore at the 5'-end and a quencher (e.g., TAMRA or non-fluorescent quencher (NFQ) at the 3'-end and is longer than a primer (e.g., 20 to 30 nucleotides). Excited fluorophore transfers energy to a nearby quencher rather than emitting fluorescence (FRET=Förster or fluorescence resonance energy transfer; Chen, X., et al., Proc Natl Acad Sci USA, 94(20): 10756-61(1997)). Therefore, a normal probe does not emit any fluorescence. TaqMan probe is designed to be annealed to an internal portion of the PCR product. Preferably, TaqMan probe may be designed as an internal sequence of the 16S rRNA gene fragment, which is amplified by the sequences of SEQ ID NO: 1 and SEQ ID NO: 2.

TaqMan probe specifically hybridizes with template DNA in the annealing step, but the fluorescence of the probe is suppressed by the quencher on the probe. At the time of an elongation reaction, the TaqMan probe hybridizing with the template is decomposed by the 5' to 3' nuclease activity of Taq DNA polymerase, and thus the fluorescence dye is free from the probe and the suppression thereof is cancelled, thereby emitting fluorescence. Here, the 5'-end of the TaqMan probe needs to be placed at the downstream of the 3'-end of the elongated primer. That is, when the 3'-end of the elongated primer is elongated by template-dependent nucleic acid polymerase, the 5'-end of the TaqMan probe is cleaved by the 5' to 3' nuclease activity of the polymerase to generate a fluorescence signal of the reporter molecule.

The reporter molecule and the quencher molecule, which bind to the TaqMan probe, include a fluorophore and a non-fluorophore. Any material that is known in the art may be used as the fluorescent reporter molecule and the quencher molecule usable in the present invention, and examples thereof are as follows (numbers in parenthesis represent the maximum emission wavelength shown in nanometers): Cy2™ (506), YO-PRO™-1 (509), YOYO™-1 (509), Calcein (517), FITC (518), FluorX™ (519), Alexa™

(520), Rhodamine 110 (520), 5-FAM (522), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO1 (533), JOE (548), BODIPY530/550 (550), DiI (565), BODIPY TMR (568), BODIPY558/568 (568), BODIPY564/570 (570), Cy3™ (570), Alexa™ 546 (570), TRITC (572), Magnesium Orange™ (575), Phycoerythrin R&B (575), Rhodamine Phalloidin (575), Calcium Orange™ (576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red (615), Nile Red (628), YO-PRO™-3 (631), YOYO™-3 (631), R-phycocyanin (642), C-Phycocyanin (648), TO-PRO™-3 (660), TOTO3 (660), DiD DilC(5) (665), Cya5® (670), Thiadicarbocyanine (671), Cy5.5 (694), HEX (556), TET (536), VIC (546), BHQ-1 (534), BHQ-2 (579), BHQ-3 (672), Biosearch Blue (447), CAL Fluor Gold 540 (544), CAL Fluor Orange 560 (559), CAL Fluor Red 590 (591), CAL Fluor Red 610 (610), CAL Fluor Red 635 (637), FAM (520), Fluorescein (520), Fluorescein-C3 (520), Pulsar 650 (566), Quasar 570 (667), Quasar 670 (705), and Quasar 705 (610). The numbers in parenthesis represent the maximum emission wavelength shown in nanometers. According to a certain embodiment of the present invention, the reporter molecule and the quencher molecule include HEX, VIC, FAM, BHQ-1, and Cy5-based labels.

Appropriate reporter-quencher pairs are disclosed in literature: Pesce et al., editors, FLUORESCENCE SPECTROSCOPY (Marcel Dekker, New York, 1971); White et al., FLUORESCENCE ANALYSIS: A PRACTICAL APPROACH (Marcel Dekker, New York, 1970); Berlman, HANDBOOK OF FLUORESCENCE SPECTRA OF AROMATIC MOLECULES, 2nd EDITION (Academic Press, New York, 1971); Griffiths, COLOUR AND CONSTITUTION OF ORGANIC MOLECULES (Academic Press, New York, 1976); Bishop, editor, INDICATORS (Pergamon Press, Oxford, 1972); Haugland, HANDBOOK OF FLUORESCENT PROBES AND RESEARCH CHEMICALS (Molecular Probes, Eugene, 1992); Pringsheim, FLUORESCENCE AND PHOSPHORESCENCE (Interscience Publishers, New York, 1949); Haugland, R. P., HANDBOOK OF FLUORESCENT PROBES AND RESEARCH CHEMICALS, Sixth Edition, Molecular Probes, Eugene, Oreg., 1996; U.S. Pat. Nos. 3,996,345 and 4,351,760.

In addition, the non-fluorophore used for the reporter molecule and the quencher molecule binding to the TaqMan probe may include a minor groove binding (MGB) moiety. As used herein, the term "TaqMan MGB-conjugate probe (MGB-conjugate probe)" means TaqMan probe conjugated to MGB at the 3'-end thereof. MGB is a material that binds to the minor groove with high affinity, and includes dihydrocyclopyrroloindole tripeptide (DPI3), netropsin, distamycin, lexitropsin, mithramycin, chromomycin A3, olivomycin, anthramycin, sibiromycin, pentamidine, stilbamidine, berenil, CC-1065, Hoechst 33258, 4'-6-diamidino-2-phenylindole (DAPI), a dimer, a trimer, a tetramer, and a pentamer of CDPI, N-methylpyrrole-4-carbox-2-amide (MPC), and a dimer, a trimer, a tetramer, and a pentamer thereof, but is not delimited thereto.

The conjugation of the probe and MGB significantly increases the stability of the hybrid formed between the probe and a target thereof. More specifically, the increased stability (that is, the increase in hybridization degree) induces an increased melting temperature (Tm) of the hybrid duplex formed by the MGB-conjugate probe when compared with normal probes. Therefore, MGB stabilizes the van der Waals force to increase the melting temperature (Tm) of the MGB-conjugated probe without increasing the length of the probe, thereby making it possible to use a shorter probe (e.g., no more than 21 nucleotides) in the Taqman real-time PCR under more strict conditions.

In addition, the MGB-conjugate probe removes background fluorescence more efficiently. According to a certain embodiment of the present invention, the length of the TaqMan MGB-conjugate of the present invention includes 15-21 nucleotides, but is not limited thereto.

According to a certain embodiment of the present invention, the 5'-end of the probe of the present invention may be labeled with one fluorophore selected from the group consisting of FAM, VIC, HEX, and CY5, and the 3'-end thereof may be modified with one quencher selected from the group consisting of BHQ-1, BHQ-2, and MGB.

More specifically, the sequence of SEQ ID NO: 3 of the present invention employs HEX as a fluorophore at the 5'-end and BHQ-1 as a fluorophore at the 3'-end; the sequence of SEQ ID NO: 4 of the present invention employs VIC as a fluorophore at the 5'-end and MGB as a fluorophore at the 3'-end; the sequences of SEQ ID NO: 9 and SEQ ID NO: 10 of the present invention employ FAM as a fluorophore at the 5'-end and BHQ-1 as a fluorophore at the 3'-end; and the sequence of SEQ ID NO: 13 of the present invention employs Cy5 as a fluorophore at the 5'-end and BHQ-2 as a fluorophore at the 3'-end.

According to a certain embodiment of the present invention, the concentration of the TaqMan MGB-conjugate probe is 50-900 nM, more specifically, 100-600 nM, still more specifically, 150-400 nM, and still more specifically 200-300 nM.

The target nucleic acid used herein includes, but is not particularly limited to, DNA (gDNA or cDNA) or RNA molecule, and more preferably gDNA. In cases where the target nucleic acid is the RNA molecule, the RNA molecule is used through reverse transcription into cDNA. The target nucleic acid includes, for example, nucleic acids of prokaryotic cells, nucleic acids of eukaryotic cells (e.g., protozoa, parasites, fungi, yeasts, higher plants, lower animals, and higher animals including mammals and human beings), nucleic acids of viruses (e.g., Herpes virus, HIV, influenza virus, Epstein-Barr virus, hepatitis virus, polio virus, etc.), or viroid nucleic acids, and more specifically includes nucleic acids of eukaryotic cells.

The annealing or hybridization of the target nucleic acid to the elongated primer and probe may be conducted by the hybridizing method known in the art. Herein, appropriate hybridization conditions may be determined by a series of processes through optimized procedures. These procedures are performed by a person skilled in the art through a series of processes in order to establish protocols to be used in the laboratory. For example, the conditions, such as temperature, concentrations of components, hybridization and reaction times, buffer components, and pH and ion intensities thereof, depend on various factors including the length of oligonucleotide, the GC amount, and the target nucleotide sequence. Detailed conditions for hybridization can be confirmed in Joseph Sambrook, et al., Molecular Cloning, A Laboratory Manual, Cold Spring Harbor Laboratory Press, Cold Spring Harbor, N.Y. (2001); and M. L. M. Anderson, Nucleic Acid Hybridization, Springer-Verlag New York Inc. N.Y. (1999).

The template-dependent nucleic acid polymerase used herein is an enzyme having 5' to 3' nuclease activity. Preferably, the template-dependent nucleic acid polymerase used herein is DNA polymerase. DNA polymerases typically have 5' to 3' nuclease activity. The template-dependent nucleic acid polymerase used herein includes *E. coli* DNA polymerase I, thermostable DNA polymerase, and bacteriophage T7 DNA polymerase. Specifically, the template-dependent nucleic acid polymerase is a thermostable DNA polymerase that can be obtained from various bacteria species, and includes DNA polymerases of *Thermus aquaticus* (Taq), *Thermus thermophilus* (Tth), *Thermus filiformis, Thermis flavus, Thermococcus literalis, Pyrococcus furiosus* (Pfu), *Thermus antranikianii, Thermus caldophilus, Thermus chliarophilus, Thermus flavus, Thermus igniterrae, Thermus lacteus, Thermus oshimai, Thermus ruber, Thermus rubens, Thermus scotoductus, Thermus silvanus, Thermus* species Z05, *Thermus* species sps 17, *Thermus thermophilus, Thermotoga maritima, Thermotoga neapolitana* and *Thermosipho africanus.*

The term "template-dependent elongation reaction" catalyzed by the template-dependent nucleic acid polymerase means the reaction of synthesizing the nucleotide sequence complementary to the sequence of the template.

According to a certain embodiment of the present invention, the real-time PCR of the present invention is conducted by the TaqMan probe method.

According to a certain embodiment of the present invention, the minimum DNA amount for the detection or quantification of *Mycobacterium tuberculosis* or nontuberculous mycobacteria through the real-time PCR of the present invention is 1 ng or less, more specifically, 100 fg or less, and still more specifically, 50 fg.

Advantageous Effects

Features and advantages of the present invention are summarized as follows.

(a) The present invention is directed to a method for specifically detecting *Mycobacterium tuberculosis* and nontuberculous mycobacteria by simultaneously amplifying and analyzing three target genes using various primers and probes, and to a diagnostic kit using the same.

(b) The method of the present invention can selectively detect *Mycobacterium tuberculosis* and nontuberculous mycobacteria with very high efficiency through multiplex real-time polymerase chain reaction (PCT) using target genes (specifically, IS6110, 16S rRNA, and β-actin)-specific primers and probes.

(c) Further, the kit of the present invention can detect the target genes in a sample conveniently and efficiently through multiplex real-time PCT.

(d) Accordingly, the method and kit of the present invention can selectively and easily detect the infection or not of the sample with *Mycobacterium tuberculosis* and nontuberculous mycobacteria, and can be applied to the treatment of diseases more accurately based on these.

MODE FOR CARRYING OUT THE INVENTION

Figure 1:
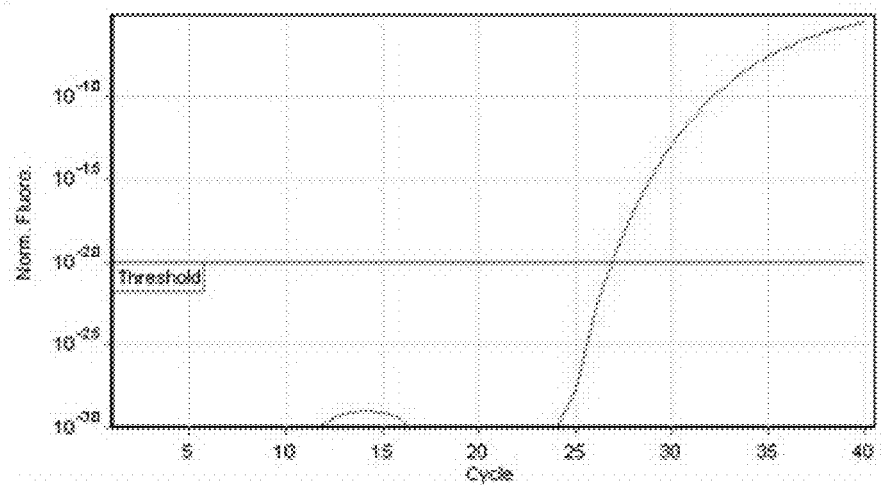
FIG. 1 illustrates fluorescent results of standard strain *M. xenopi* KMRC 4200, as a nontuberculous *mycobacterium*, using the primer pair and probe of the present invention. Y axis represents fluorescent intensity (Norm. Fluro.) that is corrected according to the amplification cycle. A, green channel (nontuberculous *mycobacterium*); B yellow channel (*Mycobacterium tuberculosis*); and C, red channel (internal control, β-actin)
Figure 1:
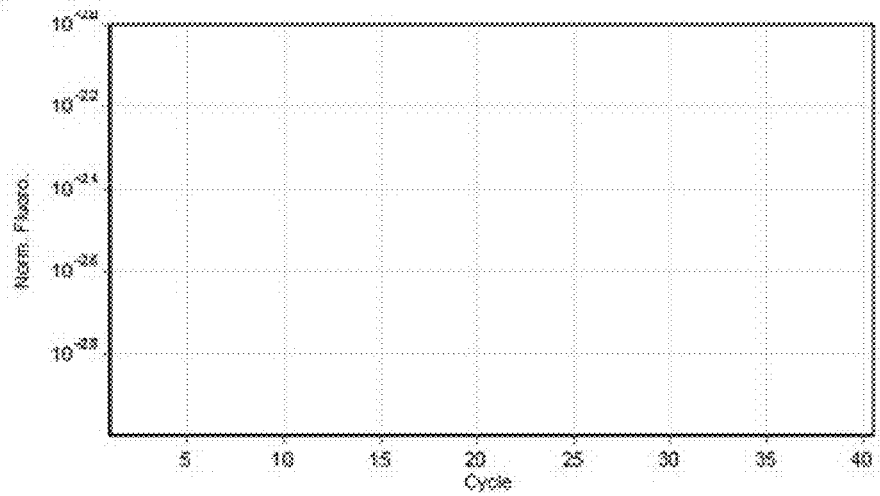
Figure 1:
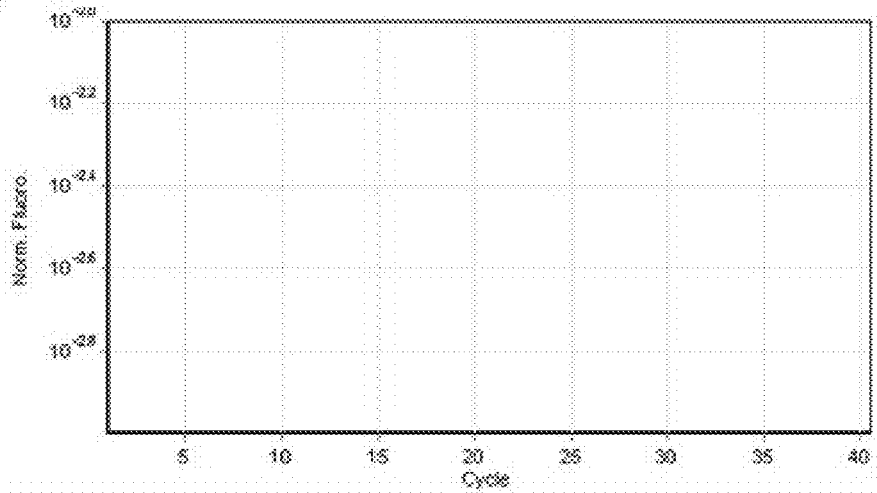

Hereinafter, the present invention will be described in detail with reference to examples. These examples are only for illustrating the present invention more specifically, and it will be apparent to those skilled in the art that the scope of the present invention is not limited by these examples.

EXAMPLES

Materials and Methods

Strains

Herein, 186 *Mycobacterium tuberculosis* strains, 78 nontuberculous mycobacteria strains, and 68 *Mycobacterium* standard strains were used. These strains were detected from liquid media (MGIT *Mycobacterium* media) or solid media (Ogawa media), or directly detected from sputum sample. The used standard strains are as follows. *M. abscesses* ATCC 19977, *M. acapulcensis* KCTC 9501, *M. africanum* ATCC 25420, *M. agri* KCTC 9502, *M. alvei* KCTC 19709, *M. asiaticum* KCTC 9503, *M. aurum* KCTC 19457, *M. austroafricanum* KCTC 9504, *M. avium* ATCC 25291, *M. bolletii* KCTC 19281, *M. botniense* KCTC 19646, *M. Bovis* ATCC 19210, *M. brumae* KCTC 19711, *M. celatum* ATCC 51131, *M. chelonae* subsp *chelonae* KCTC 9505, *M. chlorophenolicum* KCTC 19089, *M. chubuense* KCTC 19712, *M. diernhoferi* KCTC 9506, *M. fallax* KCTC 9508, *M. flavescens* ATCC 14474, *M. fortuitum* ATCC 6841, *M. frederiksbergense* KCTC 19100, *M. gadium* ATCC 27726, *M. gastri* ATCC 15754, *M. gilvum* KCTC 19423, *M. goodii* ATCC BAA-955, *M. gordonae* KCTC 9513, *M. haemophilum* ATCC 29548, *M. hassiacum* ATCC 700660, *M. interjectum* ATCC 51457, *M. intermedium* ATCC 51848, *M. intracellulare* ATCC 13950, *M. intracellulare* KCTC 9514, *M. kansasii* ATCC 12478, *M. lentiflavum* KMRC 70087, *M. malmoense* ATCC 29571, *M. mantobense* KCTC 9977, *M. marinum* ATCC 927, *M. massiliense* KCTC 19086, *M. microti* ATCC 19422, *M. moriokaense* KCTC 9516, *M. mucogenicum* KCTC 19088, *M. neoaurum* KCTC 19096, *M. nonchromogenicum* ATCC 19530, *M. obuense* KCTC 19097, *M. parascrofulaceum* KCTC 9979, *M. peregrinum* KCTC 9615, KMRC 75002, *M. phlei* KCTC 9689, *M. porcinum* KCTC 9517, *M. pulveris* KCTC 9518, *M. scrofulaceum* ATCC 19981, *M. septicum* ATCC 700731, *M. simiae* ATCC 25275, *M. shimoidei* ATCC 27962, *M. smegmatis* KCTC 9108, *M. szulgai* KCTC 9520, KMRC 31125, *M. terrae* KCTC 9614, *M. triplex* ATCC 700071, *M. triviale* KMRC 70093, *M. tuberculosis* ATCC 25177, ATCC 27294, *M. ulcerans* ATCC 19423, *M. vaccae* KCTC 19087, *M. vanbaalenii* KCTC 9966, *M. wolinskyi* ATCC 700010, and *M. xenopi* KMRC 42001.

Strain Culture and DNA Extraction

ATCC and KCTC strains were used in liquid media and KMRC strains were cultured in solid media.

DNA of the mycobacteria cultured in the liquid media was extracted as follows. 500 μl of liquid was taken from the MGIT mycobacteria culture tube, placed in 1.5 ml tube, and centrifuged at 14,000 rpm for 5 minutes. After the centrifugation, supernatant was discarded, and 300 μl of sterile distilled water was added to pellets, followed by heating in boiling water for 10 minutes. After heating in the boiling water, centrifugation was performed at 14,000 rpm for 5 minutes. The thus obtained supernatant was used as s DNA template for a polymerase chain reaction (PCR).

DNA of the mycobacteria cultured in the solid media was extracted as follows. 500 μl of sterile distilled water is placed in 1.5 ml tube, and 1 loop was taken from the solid media and dissolved in sterile distilled water. The tube was heated in boiling water for 10 minutes, and centrifuged at 14,000 rpm for 5 minutes. The thus obtained supernatant was used as a DNA template of PCR.

The sputum sample was treated as follows. The sputum was liquefied by adding 1N NaOH at the same amount as the sputum contained in the 15 ml or 50 ml tube, followed by being left for 10 minutes. After centrifugation at 14,000 rpm for 2 minutes, supernatant was discarded, and 1 ml of sterile distilled water was added to pellets. The mixture was well stirred for 10 seconds, and then centrifuged at 14,000 rpm for 2 minutes, thereby removing supernatant. 1 ml of sterile distilled water was added to the remaining pellets, and the mixture was stirred well for 10 seconds, followed by centrifugation at 14,000 rpm for 2 minutes, and then the supernatant was discarded. After that, 100 μl of 5% chelex resin (Biorad, USA) was added to the remaining pellets, and 1 μl of 10 mg/ml proteinase K was added, and then the mixture was well stirred. After being left at 56° C. for 15 minutes, and the mixture was well stirred, and then heated in boiling water for 10 minutes. After being heated in the boiling water, the resultant material was centrifuged at 14,000 rpm for 5 minutes. Then, the thus obtained supernatant was used as a DNA template of PCR.

Based on the sequence alignment, the present inventors found the regions of interest, and fabricated primers or probes using the Primer 3 program (http://frodo.wi.mit.edu/primer3/) or by hand. More specifically, 16S rRNA gene of the *Mycobacterium* species that can be obtained from the database of NCBI was sequenced, and the nucleotide sequence regions specific to the nontuberculous mycobacteria were identified from the hypervariable regions, thereby designing primers and probes. The real-time PCR primers and probes designed and used in the present study are shown in table 1.

TABLE 1

| Target gene | | Sequence (5'→3') | Expected size (bp) |
|---|---|---|---|
| IS6110 | Forward primer | atggcgaactcaagga gca (SEQ ID NO: 1) | 93 |
| | Reverse primer | cctcacggttcagggt tagc (SEQ ID NO: 2) | |
| | Taqman probe | Hex-ttacggtgcccg caaagtgt-BHQ1 (SEQ ID NO: 3) or VIC-ccaactacggtg tttacg-MGB (SEQ ID NO: 4) | |

TABLE 1-continued

| Target gene | | Sequence (5'→3') | Expected size (bp) |
|---|---|---|---|
| 16S rRNA | Forward primer | ttktggtggaaagctt ttgc, (SEQ ID NO: 5) tggtggaaagcgtttg gt, (SEQ ID NO: 6) or tggtgwgtggtgcaaa gctt (SEQ ID NO: 7) | 146 |
| | Reverse primer | cgtaggagtctgggcc gta (SEQ ID NO: 8) | |
| | Taqman probe | FAM-cctgagagggtg wccggcc-BHQ1, (SEQ ID NO: 9) or FAM-ctgtgggatgag cccgc-BHQ1 (SEQ ID NO: 10) | |
| β-actin | Forward primer | aactggaacggtgaag gtg (SEQ ID NO: 11) | 148 |
| | Reverse primer | tggcaagggacttcct gta (SEQ ID NO: 12) | |
| | Taqman probe | Cy5-agtcggttggag cgagcatc-BHQ2 (SEQ ID NO: 13) | |

Multiplex Real-Time PCR

Multiplex real-time polymerase chain reaction was performed by Rotor-Gene Q (QIAGEN Inc., Germantown, Md., USA) using Rotor-Gene multiplex PCR Kit (QIAGEN Inc., Germantown, Md., USA). PCR conditions were as follows: (a) a pre-denaturation step, 95° C. for 5 minutes; and (b) 40 cycles, each cycle consisting of 95° C. for 15 seconds (denaturation step), and 64° C. for 15 seconds (annealing and elongation steps). Here, the composition of reactants for performing the multiplex real-time polymerase chain reaction is shown in table 2 below. The following primer-probe mix included 10 pmole/μl forward primer, 10 pmole/μl reverse primer, and 4 pmole/μl probe in order to detect target genes of *Mycobacterium tuberculosis* and non-tuberculous *mycobacterium*. Therefore, 1.25 it of the primer-probe mix, which was used to detect *Mycobacterium tuberculosis* complex (MTC), included 12.5 pmole of each of forward primer and reverse primer and 5 pmole of probe. However, in order to detect a target gene used as an internal control (IC), the forward primer and reverse primer had 6.7 pmole/μl for each, and the probe had 2.7 pmole/μl. Since the total volume of the reactants for performing the polymerase chain reaction was 25 μl, the concentrations of primers for detecting *Mycobacterium tuberculosis* and nontuberculous *mycobacterium* were 0.5 μM (12.5 pmole/25 μl) and the concentration of the probe therefor was 0.2 μM (5 pmole/25 μl), and the concentrations of primers for detecting a target gene as an internal control were 0.27 μM (6.7 pmole/25 μl) and the concentration of the probe therefor was 0.11 μM (2.7 pmole/25 μl). The concentrations of forward and reverse primers and probe of NTM were the same as in MTC.

TABLE 2

Composition and concentration of reactants for performing polymerase chain reaction

| Components | | Volume (μl) | Concentration |
|---|---|---|---|
| 2X Rotor-Gene Multiplex PCR Master Mix | | 12.5 | 1X |
| Primer-Probe Mix | Primer (10 pmole/μl): | 1.25 | 0.5 μM: |
| | IC Primer (6.7 pmole/μl) | | 0.27 μM |
| | Probe (4 pmole/μl): | | 0.2 μM: |
| | IC Probe (2.7 pmole/μl) | | 0.11 μM |
| Nuclease-deficient water | | 6.25 | — |
| Sample DNA template | | 5 | — |
| Total | | 25 | — |

The fluorescence generated by the probe in the binding and elongation steps during the multiplex real-time polymerase chain reaction was measured by Rotor-Gene Q (QIAGEN Inc., Germantown, Md., USA). In the multiplex real-time polymerase chain reaction, the fluorescence is detected and quantified in real time for every cycle of the real-time polymerase chain reaction using DNA polymerase and the principle of fluorescence resonance energy transfer (FRET). The color development of FAM™ was assigned to be displayed in a green channel (510±5 nm), Hex™ or VIC™ in a yellow channel (555±5 nm), and Cy5™ in a red channel (660±10 nm) on the real-time monitor. The fluorescence was observed in the green channel, yellow channel, and red channel.

Results

Figure 2:
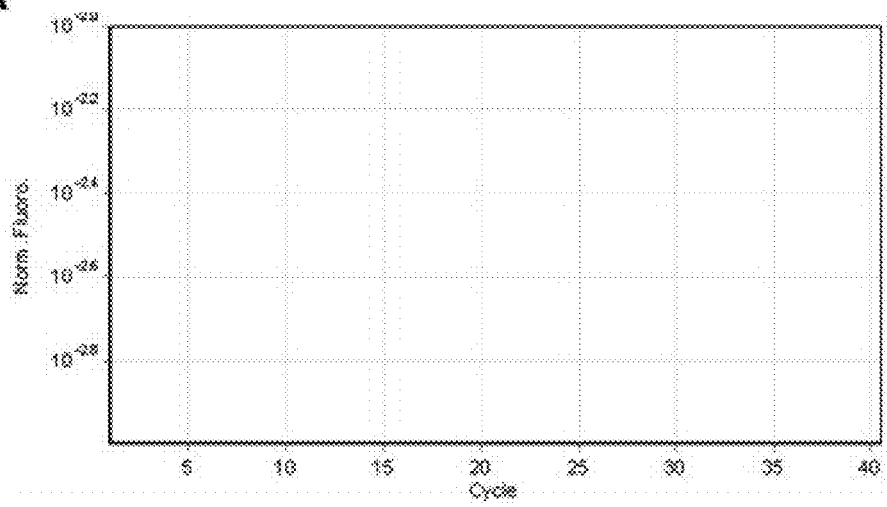
FIG. 2 illustrates fluorescent results of *Mycobacterium tuberculosis* in clinical sample *Mycobacterium tuberculosis* using the primer pair and probe of the present invention. Y axis represents fluorescent intensity (Norm. Fluro.) that is corrected according to the amplification cycle. A, green channel (nontuberculous *mycobacterium*); B yellow channel (*Mycobacterium tuberculosis*); and C, red channel (internal control, β-actin)
Figure 2:
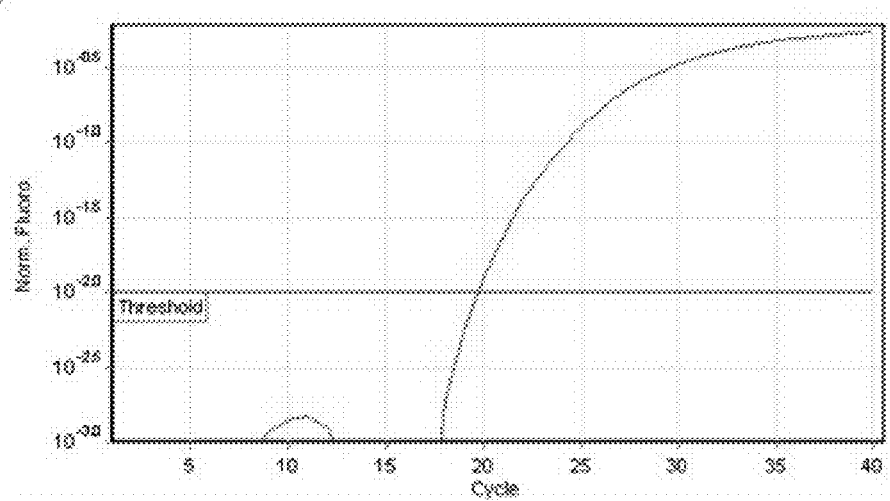
Figure 2:
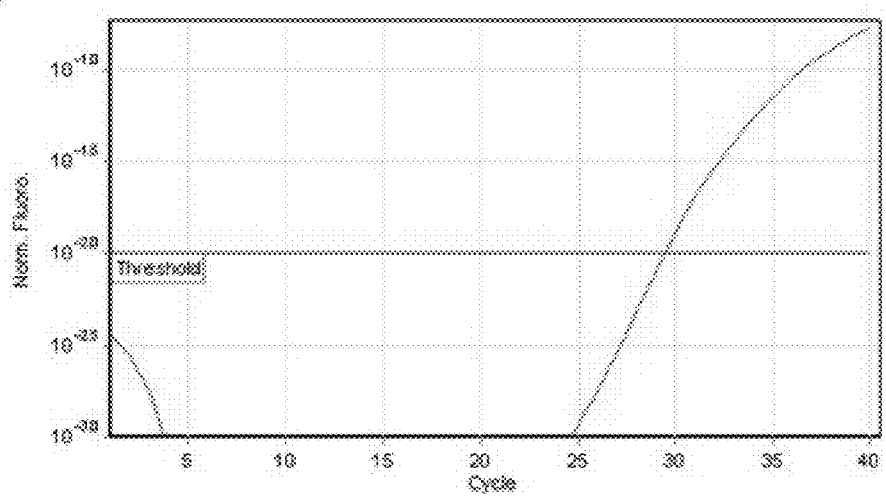

The fluorescence was observed in only the green channel for nontuberculous *mycobacterium* standard strain *M. xenopi* KMRC 42001 (FIG. 1). The fluorescence was observed in the yellow channel and red channel for *Mycobacterium tuberculosis* isolated from the clinical sample since human β-actin gene is included therein (FIG. 2).

Figure 3:
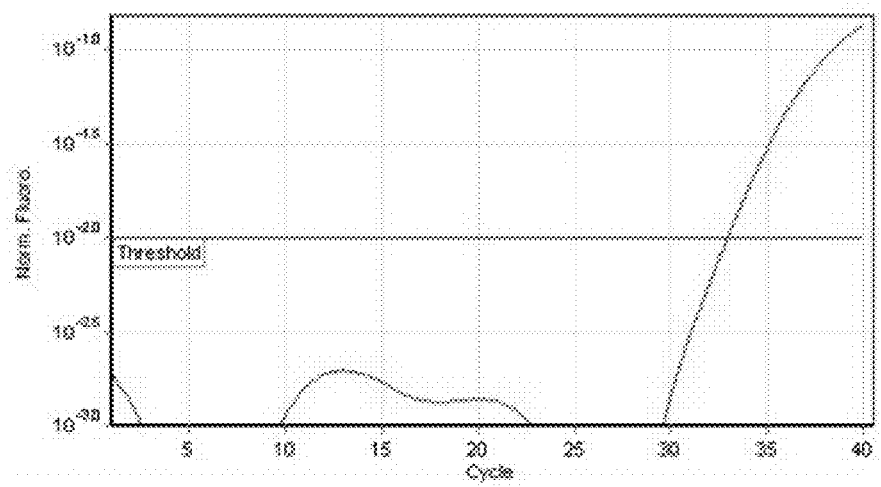
FIG. 3 illustrates fluorescent results of clinical sample, in which *Mycobacterium tuberculosis* and nontuberculous mycobacterium are mixed, using the primer pair and probe of the present invention. Y axis represents the fluorescent intensity (Norm. Fluro.) that is corrected according to the amplification cycle. A, green channel (nontuberculous *mycobacterium*); B yellow channel (*Mycobacterium tuberculosis*); and C, red channel (internal control, β-actin)
Figure 3:
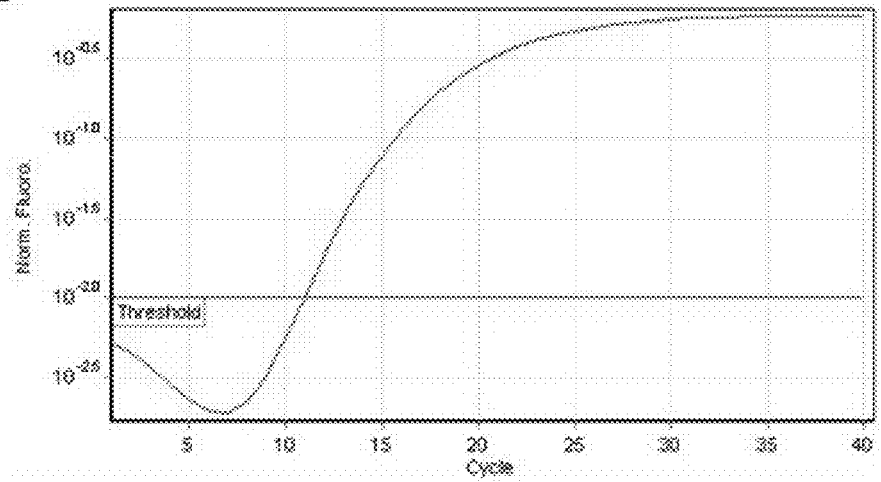
Figure 3:
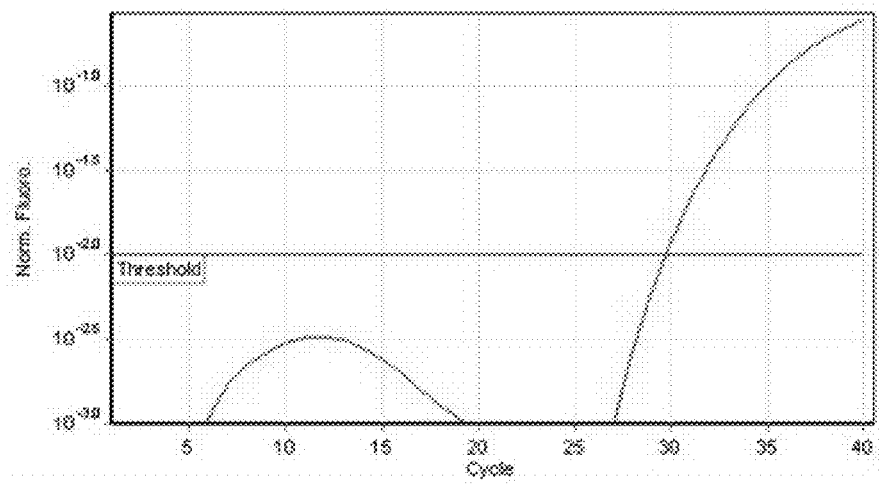

The fluorescence was detected in all the channels (green, yellow, and red) when *Mycobacterium tuberculosis* and nontuberculous *mycobacterium* are mixed in the clinical sample (FIG. 3).

Although the present invention has been described in detail with reference to the specific features, it will be apparent to those skilled in the art that this description is only for one embodiment and does not limit the scope of the present invention. Thus, the substantial scope of the present invention will be defined by the appended claims and equivalents thereof.

The invention claimed is:

1. A selective detection method of *Mycobacterium tuberculosis* and nontuberculous mycobacteria, the method comprising:
   (a) preparing a sample;
   (b) amplifying a target nucleotide sequence in the sample using: (i) a *Mycobacterium tuberculosis* detection set comprising a primer pair including a primer of SEQ ID NO: 1 and a primer of SEQ ID NO: 2, and at least one probe selected from the group consisting of SEQ ID NO: 3 and SEQ ID NO: 4; and (ii) a nontuberculous mycobacteria detection set comprising a primer pair including at least one primer selected from the group consisting of SEQ ID NO: 5, SEQ ID NO: 6, and SEQ ID NO: 7 and a primer of SEQ ID NO: 8, and at least one probe selected from the group consisting of SEQ ID NO: 9 and SEQ ID NO: 10; and
   (c) analyzing results of the amplification, wherein the amplification is performed by multiplex real-time PCR.

2. The method of claim 1, wherein the sample is sputum, blood, saliva, or urine.

3. The method of claim 1, wherein the probe has a label bound thereto, and wherein in step (c), the results of the amplification are analyzed by detecting a signal generated from the probe.

4. The method of claim 1, wherein the real-time PCR is performed by a TaqMan probe method.

5. The method of claim 1, wherein the step (b) further comprises an internal control detection set.

6. The method of claim 1, wherein the 5'-ends of the nucleotide sequences of SEQ ID NOs: 3, 4, 9, and 10 are labeled with a fluorophore selected from the group consisting of FAM, VIC, HEX, and CY5, and the 3'-ends thereof are modified with a quencher selected from the group consisting of BHQ-1, BHQ-2, and MGB.

* * * * *

SEQUENCE LISTING

<160> NUMBER OF SEQ ID NOS: 13

<210> SEQ ID NO 1
<211> LENGTH: 19
<212> TYPE: DNA
<213> ORGANISM: Artificial Sequence
<220> FEATURE:
<223> OTHER INFORMATION: IS6110 forward primer

<400> SEQUENCE: 1
atggcgaact caaggagca                                         19

<210> SEQ ID NO 2
<211> LENGTH: 20
<212> TYPE: DNA
<213> ORGANISM: Artificial Sequence
<220> FEATURE:
<223> OTHER INFORMATION: IS6110 reverse primer

<400> SEQUENCE: 2
cctcacggtt cagggttagc                                        20

<210> SEQ ID NO 3
<211> LENGTH: 20
<212> TYPE: DNA
<213> ORGANISM: Artificial Sequence
<220> FEATURE:
<223> OTHER INFORMATION: IS6110 Taqman probe 1

<400> SEQUENCE: 3
ttacggtgcc cgcaaagtgt                                        20

<210> SEQ ID NO 4
<211> LENGTH: 18
<212> TYPE: DNA
<213> ORGANISM: Artificial Sequence
<220> FEATURE:
<223> OTHER INFORMATION: IS6110 Taqman probe 2

<400> SEQUENCE: 4
ccaactacgg tgtttacg                                                18

<210> SEQ ID NO 5
<211> LENGTH: 20
<212> TYPE: DNA
<213> ORGANISM: Artificial Sequence
<220> FEATURE:
<223> OTHER INFORMATION: 16S rRNA forward primer 1

<400> SEQUENCE: 5
ttktggtgga aagctttttgc                                             20

<210> SEQ ID NO 6
<211> LENGTH: 18
<212> TYPE: DNA
<213> ORGANISM: Artificial Sequence
<220> FEATURE:
<223> OTHER INFORMATION: 16S rRNA forward primer 2

<400> SEQUENCE: 6
tggtggaaag cgtttggt                                                18

<210> SEQ ID NO 7
<211> LENGTH: 20
<212> TYPE: DNA
<213> ORGANISM: Artificial Sequence
<220> FEATURE:
<223> OTHER INFORMATION: 16S rRNA forward primer 3

<400> SEQUENCE: 7
tggtgwgtgg tgcaaagctt                                              20

<210> SEQ ID NO 8
<211> LENGTH: 19
<212> TYPE: DNA
<213> ORGANISM: Artificial Sequence
<220> FEATURE:
<223> OTHER INFORMATION: 16S rRNA reverse primer

<400> SEQUENCE: 8
cgtaggagtc tgggccgta                                               19

<210> SEQ ID NO 9
<211> LENGTH: 19
<212> TYPE: DNA
<213> ORGANISM: Artificial Sequence
<220> FEATURE:
<223> OTHER INFORMATION: 16S rRNA Taqman probe 1

<400> SEQUENCE: 9
cctgagaggg tgwccggcc                                               19

<210> SEQ ID NO 10
<211> LENGTH: 17
<212> TYPE: DNA
<213> ORGANISM: Artificial Sequence
<220> FEATURE:
<223> OTHER INFORMATION: 16S rRNA Taqman probe 2

<400> SEQUENCE: 10
ctgtgggatg agcccgc                                                 17

<210> SEQ ID NO 11
<211> LENGTH: 19
<212> TYPE: DNA
<213> ORGANISM: Artificial Sequence

```
<220> FEATURE:
<223> OTHER INFORMATION: beta-actin forward primer

<400> SEQUENCE: 11
aactggaacg gtgaaggtg                                              19

<210> SEQ ID NO 12
<211> LENGTH: 19
<212> TYPE: DNA
<213> ORGANISM: Artificial Sequence
<220> FEATURE:
<223> OTHER INFORMATION: beta-actin reverse primer

<400> SEQUENCE: 12
tggcaaggga cttcctgta                                              19

<210> SEQ ID NO 13
<211> LENGTH: 20
<212> TYPE: DNA
<213> ORGANISM: Artificial Sequence
<220> FEATURE:
<223> OTHER INFORMATION: beta-actin Taqman probe

<400> SEQUENCE: 13
agtcggttgg agcgagcatc                                             20
```